(12) United States Patent
Taniguchi et al.

(10) Patent No.: US 7,419,932 B2
(45) Date of Patent: Sep. 2, 2008

(54) METHOD FOR PRESERVING CATALYST

(75) Inventors: Yoshiyuki Taniguchi, Hiroshima (JP);
Toru Kuroda, Hiroshima (JP);
Hideyasu Takezawa, Hiroshima (JP);
Yasuhiro Kabu, Hiroshima (JP)

(73) Assignee: Mitsubishi Rayon Co., Ltd., Tokyo (JP)

( * ) Notice: Subject to any disclaimer, the term of this patent is extended or adjusted under 35 U.S.C. 154(b) by 233 days.

(21) Appl. No.: 10/542,018

(22) PCT Filed: Jan. 9, 2004

(86) PCT No.: PCT/JP2004/000102

§ 371 (c)(1),
(2), (4) Date: Jul. 11, 2005

(87) PCT Pub. No.: WO2004/062798

PCT Pub. Date: Jul. 29, 2004

(65) Prior Publication Data

US 2006/0128561 A1    Jun. 15, 2006

(30) Foreign Application Priority Data

Jan. 9, 2003   (JP)   ............... 2003-003115

(51) Int. Cl.
*B01J 27/188* (2006.01)
*B01J 27/19* (2006.01)
*B01J 27/192* (2006.01)
*B01J 27/185* (2006.01)
*B01J 27/182* (2006.01)
*B01J 27/057* (2006.01)
*B01J 23/00* (2006.01)
*C07C 51/16* (2006.01)
*C07C 51/235* (2006.01)
*C07C 51/295* (2006.01)
*C07C 45/00* (2006.01)

(52) U.S. Cl. ............. 502/210; 502/211; 502/212; 502/213; 502/214; 502/215; 502/300; 502/313; 502/317; 502/319; 502/325; 568/470

(58) Field of Classification Search ......... 502/210–215, 502/300–355; 562/632, 535, 539; 568/470
See application file for complete search history.

(56) References Cited

U.S. PATENT DOCUMENTS

| | | |
|---|---|---|
| 2003/0162997 A1 * | 8/2003 | Uhara et al. ............... 562/532 |
| 2004/0116284 A1 * | 6/2004 | Stevenson et al. .......... 502/311 |
| 2004/0192973 A1 * | 9/2004 | Liang et al. ............... 568/470 |

FOREIGN PATENT DOCUMENTS

| | | |
|---|---|---|
| JP | 58-156351 | 9/1983 |
| JP | 60-232247 | 11/1985 |
| JP | 06-007685 | 1/1994 |
| JP | 06-233938 | 8/1994 |
| JP | 06-262081 | 9/1994 |
| JP | 08-332387 | 12/1996 |
| JP | 2003-010695 | 1/2003 |
| WO | 02/064541 | 8/2002 |

* cited by examiner

*Primary Examiner*—Jerry Lorengo
*Assistant Examiner*—Patricia L Hailey
(74) *Attorney, Agent, or Firm*—Oblon, Spivak, McClelland, Maier & Neustadt, P.C.

(57) ABSTRACT

The method for preserving a catalyst of the present invention is characterized in that, in a process for continuously producing an objective product by a vapor phase oxidation reaction using a phosphorus-molybdenum-vanadium catalyst containing phosphorus, molybdenum and vanadium, the phosphorus-molybdenum-vanadium catalyst retained in a reactor is maintained under a condition of a water content of 30 mg or less per 1 g of catalyst dry weight, before the start of the reaction or during the stop of the reaction. By this, deterioration of the catalyst retained in the reactor can be simply prevented.

28 Claims, No Drawings

METHOD FOR PRESERVING CATALYST

TECHNOLOGICAL FIELD

The present invention relates to a method for preserving a catalyst, more specifically, in a process for continuously producing an objective product by a vapor phase oxidation reaction using a phosphorus-molybdenum-vanadium catalyst, to a method for preserving the catalyst with preventing the deterioration after filling a reactor with a catalyst or during the stop of operation.

BACKGROUND TECHNOLOGY

Conventionally, a phosphorus-molybdenum-vanadium catalyst containing phosphorus, molybdenum and vanadium is used in a method for producing methacrylic acid from methacrolein by catalytic oxidation in a vapor phase, and other methods. Industrially, the phosphorus-molybdenum-vanadium catalyst is filled in a multi-tubular heat exchange type reactor, and methacrylic acid is produced from methacrolein at a reaction temperature of about 250 to 400° C. in a fixed bed reactor.

A phosphorus-molybdenum-vanadium catalyst is used in a reaction over relatively a long period of time, and its deterioration with the passage of time in the reaction is known. It is desirable that the catalyst is able to retain catalytic activity over a long period stably from the industrial standpoint and economical standpoint. Therefore, producing methods of the catalyst and catalyst formulations have been eagerly improved.

Also, there are various suggestions on a method for regenerating the deteriorated catalyst. For example, Japanese Patent Application Laid-Open No. 60-232247 discloses a method for regenerating a catalyst in which a catalyst having deteriorated activity is dispersed in an aqueous medium and treated with a nitrogen-containing hetero-cyclic compound. Japanese Patent Application Laid-Open No. 6-233938 discloses a method for regenerating a used catalyst by the action of an oxidizer or oxidation method, and the dissolving action of an ammonia aqueous solution containing added acetic acid and/or its ammonium salt, and subsequent drying and calcination, wherein the content of a metal component is quantitatively measured, and the metal component is replenished so that this content is retuned to its initial value. Both of the methods described in Japanese Patent Application Laid-Open Nos. 60-232247 and 6-233938 are methods for regenerating a catalyst removed from a reactor.

On the other hand, methods of regenerating a catalyst in a reactor are also variously suggested. For example, Japanese Patent Application Laid-Open No. 58-156351 discloses a method for regenerating a catalyst in which a catalyst having lowered activity is treated at a temperature of 70 to 240° C. in a gas flow having a water vapor partial pressure of 10 vol % or more. Japanese Patent Application Laid-Open No. 6-7685 discloses a method for regenerating a deteriorated catalyst in a reactor in which a thermal treatment of the catalyst is conducted at a temperature of 300 to 410° C. for 0.5 to 50 hours under flow of an oxidizing gas containing molecular oxygen in an amount of at least 0.1 vol %.

Further, Japanese Patent Application Laid-Open No. 8-332387 discloses a method for regenerating a catalyst in which a catalyst composed of a mixed oxide of vanadium and phosphorus used in a method for oxidizing a hydrocarbon having 4 carbon atoms to produce maleic anhydride is allowed to contact with a water vapor in an amount of 0.02 to 30 g per 1 g of the catalyst at 300 to 600° C. Japanese Patent Application Laid-Open No. 6-262081 discloses a method for regenerating a catalyst in which a molybdenum-vanadium oxidation catalyst having catalytic activity decreased in a cause of use in a process for producing acrylic acid from acrolein or a reaction raw material gas containing acrolein by catalytic oxidation in a vapor phase is thermally treated at a temperature in the range of 300 to 450° C. under flow of a mixed gas containing at least 3 vol % of molecular oxygen and at least 0.1 vol % of water vapor.

To prevent deterioration of a catalyst and to use the catalyst stably over a long period is industrially important matter.

DISCLOSURE OF THE INVENTION

An object of the present invention is to provide a simple catalyst preserving method having a process for continuously producing an objective product by a vapor phase oxidation reaction using a phosphorus-molybdenum-vanadium catalyst in which deterioration can be prevented before the start of the reaction using a catalyst retained in a reactor or during the stop of the reaction.

The present invention relates to a method for preserving a catalyst comprising maintaining a phosphorus-molybdenum-vanadium catalyst containing phosphorus, molybdenum and vanadium retained in a reactor under a condition of a water content of 30 mg or less per 1 g of catalyst dry weight, before the start of the reaction or during the stop of the reaction.

Further, the present invention relates to the above-mentioned method for preserving a catalyst, wherein a retaining temperature of said catalyst is 0° C. or higher and not higher than the calcination temperature in catalyst production, and said water concentration in gas in the reactor is 1 vol % or less.

Further, the present invention relates to the above-mentioned method for preserving a catalyst, wherein said retaining temperature of the catalyst is 15° C. or higher and 150° C. or lower, and said water concentration in gas in the reactor is 0.5 vol % or less.

Further, the present invention relates to the above-mentioned method for preserving a catalyst, wherein said temperature of the catalyst is retained 0° C. or higher and not higher than the calcination temperature in catalyst production, and a gas having a water concentration of 0.8 vol % or less and containing substantially no component lowering a catalytic performance is allowed to pass through in said reactor.

Further, the present invention relates to the above-mentioned method for preserving a catalyst, wherein said temperature of the catalyst is retained 15° C. or higher and 150° C. or lower, and a gas having a water concentration of 0.5 vol % or less and containing substantially no component lowering a catalytic performance is allowed to pass through in said reactor.

Further, the present invention relates to the above-mentioned method for preserving a catalyst, wherein the gas to be passed through in the reactor is an inert gas or oxidizing gas.

Further, the present invention relates to the above-mentioned method for preserving a catalyst, wherein said phosphorus-molybdenum-vanadium catalyst is a catalyst used in catalytic oxidation of methacrolein to methacrylic acid in a vapor phase.

Further, the present invention relates to the above-mentioned method for preserving a catalyst, wherein said phosphorus-molybdenum-vanadium catalyst is represented by the following formula (I):

$$P_a Mo_b V_c Cu_d X_e Y_f Z_g O_h \qquad (I)$$

wherein, P, Mo, V, Cu and O represent phosphorus, molybdenum, vanadium, copper and oxygen, respectively, X represents at least one element selected from the group consisting of antimony, bismuth, arsenic, germanium, zirconium, tellurium, silver, selenium, silicon, tungsten and boron, Y represents at least one element selected from the group consisting of iron, zinc, chromium, magnesium, tantalum, cobalt, manganese, barium, gallium, cerium and lanthanum, and Z represents at least one element selected from the group consisting of potassium, rubidium and cesium. a, b, c, d, e, f, g and h represent atom ratio of each element, and when b=12, then, a=0.5 to 3, c=0.01 to 3, d=0.01 to 2, e=0 to 3, f=0 to 3, g=0.01 to 3, and h represents atom ratio of oxygen necessary for satisfying atomic valence of each component.

Still further, the present invention relates to the above-mentioned method for preserving a catalyst, wherein said phosphorus-molybdenum-vanadium catalyst is preserved in dark ambient.

BEST MODES FOR CARRYING OUT THE INVENTION

In a process for continuously producing an objective product using a catalyst filled in a reactor, the catalyst is retained in a reactor in some cases under a condition of not reaction such as from filling of a catalyst to the start of the reaction, or during the stop of operation (during the stop of the reaction) and the like. A phosphorus-molybdenum-vanadium catalyst used, for example, in producing methacrylic acid from methacrolein by catalytic oxidation in a vapor phase shows decrease in catalytic activity in some cases also before the start of the reaction or during the stop of the reaction as described above, in addition to activity decrease and, further, deactivation in the reaction.

The inventors of this application have found that a cause for activity decrease of a catalyst before the start of the reaction or during the stop of the reaction is absorption of moisture to the catalyst. It has been also found that a catalyst having activity once decreased by absorption of moisture does not show recovery of activity even if it is simply re-dried in dry air.

In the present invention, by maintaining a phosphorus-molybdenum-vanadium catalyst under a condition of a water content of 30 mg or less (including also 0 mg) per 1 g of catalyst dry weight, decrease in activity of a catalyst is prevented before the start of the reaction or during the stop of the reaction, resultantly, the catalyst can be used stably over a long period.

The water content per 1 g of dry weight of a phosphorus-molybdenum-vanadium catalyst is maintained at preferably 20 mg or less, more preferably 10 mg or less.

For maintaining the water content of a phosphorus-molybdenum-vanadium catalyst in the above-mentioned range, the catalyst retaining temperature and a water content in a gas to be contacted with the catalyst are important.

Although varying depending on the formulation of a catalyst and other preservation conditions and the like, the catalyst retaining temperature is usually not higher than the calcination temperature in catalyst production, preferably not higher than the reaction temperature, more preferably 150° C. or lower. The calcination temperature is usually about 300 to 500° C., and the reaction temperature is usually about 300 to 400° C. The catalyst retaining temperature is usually 0° C. or more, preferably 15° C. or more. It is preferable that the catalyst retaining temperature is not so high from the standpoint of thermal stability of a catalyst and economy.

Though varying depending on the formulation of a catalyst and other preservation conditions and the like, the water concentration in gas in a reactor is preferably 1 vol % or less (including also 0 vol %), more preferably 0.8 vol % or less, particularly preferably 0.5 vol % or less.

As the method for maintaining the water concentration in gas in a reactor within the above-mentioned range, there is mentioned, for example, a method in which a gas having a water concentration of 1 vol % or less, more preferably 0.8 vol % or less, particularly preferably 0.5 vol % or less and containing substantially no component lowering catalyst performance is allowed to pass through in the reactor. This method does not require big works, and even if injure of equipments or sealing failure part is present, a possibility of entering of outer air into the reactor is low. As the component lowering catalyst performance, for example, halogens, halogen-containing compounds, sulfur-containing compounds and the like are mentioned.

As the gas containing substantially no component lowering catalyst performance to be passed through in the reactor, inert gases, oxidizing gases containing oxygen, and the like are mentioned. Specifically, air, oxygen, nitrogen, combustion gas and the like are mentioned. These gases may be used singly or in admixture of two or more. When oxygen is contained, the oxygen concentration is not particularly restricted, and it is preferably 10 to 30 vol % from the standpoint of economy and safety. As the gas to be passed through in the reactor, air is preferably used from the standpoint of cost.

The water concentration in a gas to be passed through in the reactor can be controlled, for example, by lowering once the temperature of the gas and reducing the water concentration in the gas down to saturated vapor amount at this temperature. Plant air and instrument air and the like having small water concentration in gas can also be used as it is.

The amount of a gas to be passed through in the reactor is not particularly restricted providing it is an amount preventing outer air from entering into the reactor. The amount of a gas to be passed through in the reactor can be appropriately determined in view of closeness of the reactor, economy, workability and the like.

As the method for maintaining the water concentration in gas in the reactor within the above-mentioned range, there is mentioned a method in which the reactor is filled with a gas showing substantially no reactivity having a water concentration of 1 vol % or less, preferably 0.5 vol % or less (gas containing substantially no component lowering catalyst performance), then, a closing plate or the like is inserted into piping at the inlet side and outlet side of a gas in the reactor to attain closure, in addition to the above-mentioned method.

In the present invention, it is preferable to make dark ambient in the reactor and preserve a phosphorus-molybdenum-vanadium catalyst in it since deterioration in activity of a catalyst can be suppressed.

The phosphorus-molybdenum-vanadium catalyst used in the present invention is not particularly restricted providing it contains phosphorus, molybdenum and vanadium, and a phosphorus-molybdenum-vanadium catalyst used in producing methacrylic acid from methacrolein by catalytic oxidation in a vapor phase gives more excellent results. Particularly, in the case of a phosphorus-molybdenum-vanadium catalyst represented by the following formula (I), more excellent results are obtained.

$$P_aMo_bV_cCu_dX_eY_fZ_gO_h \qquad (I)$$

wherein, P, Mo, V, Cu and O represent phosphorus, molybdenum, vanadium, copper and oxygen, respectively, X represents at least one element selected from the group consisting of antimony, bismuth, arsenic, germanium, zirconium, tellurium, silver, selenium, silicon, tungsten and boron, Y represents at least one element selected from the group consisting of iron, zinc, chromium, magnesium, tantalum, cobalt, manganese, barium, gallium, cerium and lanthanum, and Z represents at least one element selected from the group consisting of potassium, rubidium and cesium. a, b, c, d, e, f, g and h represent atom ratio of each element, and when b=12, then, a=0.5 to 3, c=0.01 to 3, d=0.01 to 2, e=0 to 3, f=0 to 3, g=0.01 to 3, and h represents atom ratio of oxygen necessary for satisfying atomic valence of each component.

EXAMPLES

The present invention will be described by examples and comparative examples below, but the scope of the invention is not limited to the examples.

In examples, comparative examples and reference examples, "part(s)" mean "part(s) by weight" and "%" means "vol %" unless otherwise stated.

The reaction ratio of methacrolein, the selectivity of methacrylic acid, the yield of methacrylic acid and the water content of a catalyst were defined as described below.

Reaction ratio (%) of methacrolein=B/A×100
Selectivity (%) of methacrylic acid=C/B×100
Yield (%) of methacrylic acid=C/A×100
Water content of a catalyst (mg/g)=D/E Here, "A" represents mol number of methacrolein fed, "B" represents mol number of methacrolein reacted, and "C" represents mol number of methacrylic acid produced. "D" represents the weight of water in a catalyst (mg), and "E" represents the weight of a catalyst under dry condition, namely, catalyst dry weight (g).

Products were analyzed by gas chromatography.

The weight of a catalyst after preparation of the catalyst in reference examples, and the weight of a catalyst retained under the same preserving condition in a reactor in examples and comparative examples, was measured. Then, the catalyst was dried at 130° C. for 16 hours and the weight thereof (catalyst dry weight) was measured. A difference between them was used as the weight of water in the catalyst and the water content of the catalyst was calculated according to the above-described formula.

Reference Example 1

100 parts of ammonium paramolybdate, 2.8 parts of ammonium metavanadate and 4.8 parts of potassium nitrate were dissolved in 100 parts of pure water. While stirring this solution, a solution prepared by dissolving 8.2 parts of 85 wt % phosphoric acid in 10 parts of pure water was added to this, further, a solution prepared by dissolving 1.1 parts of telluric acid in 20 parts of pure water, and 5.4 parts of antimony trioxide were added and the mixture was heated up to 95° C. To this was added a solution prepared by dissolving 4.5 parts of copper nitrate and 3.8 parts of ferric nitrate in 30 parts of pure water, and the resulted mixture was evaporated to dryness while stirring with heating at 100° C. The resulted solid was dried at 130° C. for 16 hours, then, molded under press, and thermally treated at 380° C. for 5 hours under air flow to obtain a phosphorus-molybdenum-vanadium catalyst. The element formulation of this catalyst excepting oxygen was as shown below.

$Mo_{12}P_{1.5}V_{0.5}Fe_{0.2}Cu_{0.4}Sb_{0.8}K_{1.0}Te_{0.1}$

The water content of the catalyst was 3.7 mg-$H_2O$/g-catalyst (dry).

This catalyst was filled in a stainless steel reactor having an internal diameter of 16.1 mm and a length of 600 mm, and a reaction gas composed of 6% of methacrolein, 11% of oxygen, 30% of water vapor and 53% of nitrogen was passed through under normal pressure at a reaction temperature 285° C. for a contact time of 3.8 seconds, performing a vapor phase oxidation reaction. The product was collected and analyzed, as a result, the reaction ratio of methacrolein was 87.8%, the selectivity of methacrylic acid was 87.5%, and the yield of methacrylic acid was 76.8%.

Example 1

The same catalyst as prepared in Reference Example 1 was filled in the same stainless steel reactor as used in Reference Example 1. Then, air having a water concentration of 0.3% was passed through at 0.3 L/Hr per unit catalyst weight (g) while retaining the temperature of a catalyst layer at 20° C. for 10 days. The water content of the catalyst after maintaining for 10 days was 5.6 mg-$H_2O$/g-catalyst(dry).

The same reaction was conducted as in Reference Example 1 using this catalyst. As a result, the reaction ratio of methacrolein was 87.0%, the selectivity of methacrylic acid was 88.2%, and the yield of methacrylic acid was 76.7%.

Example 2

The same catalyst as prepared in Reference Example 1 was filled in the same stainless steel reactor as used in Reference Example 1. Then, plant air having a water concentration of about 0% (dew point −35° C.) was passed through at 0.6 L/Hr per unit catalyst weight (g) while retaining the temperature of a catalyst layer at 15° C. for 40 days. The water content of the catalyst after maintaining for 40 days was 3.8 mg-$H_2O$/g-catalyst(dry).

The same reaction was conducted as in Reference Example 1 using this catalyst. As a result, the reaction ratio of methacrolein was 86.6%, the selectivity of methacrylic acid was 88.1%, and the yield of methacrylic acid was 76.3%.

Example 3

The same catalyst as prepared in Reference Example 1 was filled in the same stainless steel reactor as used in Reference Example 1. Then, air having a water concentration of 0.2% was passed through at 0.3 L/Hr per unit catalyst weight (g) while retaining the temperature of a catalyst layer at 30° C. for 20 days. The water content of the catalyst after maintaining for 20 days was 4.2 mg-$H_2O$/g-catalyst(dry).

The same reaction was conducted as in Reference Example 1 using this catalyst. As a result, the reaction ratio of methacrolein was 86.2%, the selectivity of methacrylic acid was 88.6%, and the yield of methacrylic acid was 76.4%.

Comparative Example 1

The same catalyst as prepared in Reference Example 1 was filled in the same stainless steel reactor as used in Reference Example 1. Then, air having a water concentration of 0.9% was passed through at 0.3 L/Hr per unit catalyst weight (g) while retaining the temperature of a catalyst layer at 15° C. for 16 hours. The water content of the catalyst after maintaining for 16 hours was 44.3 mg-$H_2O$/g-catalyst(dry).

The same reaction was conducted as in Reference Example 1 using this catalyst. As a result, the reaction ratio of methacrolein was 77.4%, the selectivity of methacrylic acid was 88.2%, and the yield of methacrylic acid was 68.3%.

Comparative Example 2

The same catalyst as prepared in Reference Example 1 was filled in the same stainless reactor as used in Reference Example 1. Then, air having a water concentration of 0.9% was passed through at 0.3 L/Hr per unit catalyst weight (g) while retaining the temperature of a catalyst layer at 30° C. for 10 days. The water content of the catalyst after maintaining for 10 days was 63.7 mg-$H_2O$/g-catalyst(dry).

The same reaction was conducted as in Reference Example 1 using this catalyst. As a result, the reaction ratio of methacrolein was 60.3%, the selectivity of methacrylic acid was 80.2%, and the yield of methacrylic acid was 48.4%.

Comparative Example 3

The same catalyst as prepared in Reference Example 1 was filled in the same stainless reactor as used in Reference Example 1. Then, air having a water concentration of 0.9% was passed through at 0.3 L/Hr per unit catalyst weight (g) while retaining the temperature of a catalyst layer at 15° C. for 16 hours in the same manner as in Comparative Example 1.

This catalyst was dried at 280° C. for 5 hours under flow of instrument air having a water concentration of about 0%. The water content of the catalyst after drying was 4.0 mg-$H_2O$/g-catalyst(dry).

The same reaction was conducted as in Reference Example 1 using this catalyst. As a result, the reaction ratio of methacrolein was 77.7%, the selectivity of methacrylic acid was 88.5%, and the yield of methacrylic acid was 68.8%.

Comparative Example 4

The same catalyst as prepared in Reference Example 1 was filled in the same stainless steel reactor as used in Reference Example 1. Then, air having a water concentration of 0.9% was passed through at 0.3 L/Hr per unit catalyst weight (g) while retaining the temperature of a catalyst layer at 30° C. for 10 days in the same manner as in Comparative Example 2.

This catalyst was dried at 280° C. for 5 hours under flow of instrument air having a water concentration of about 0%. The water content of the catalyst after drying was 6.8 mg-$H_2O$/g-catalyst(dry).

The same reaction was conducted as in Reference Example 1 using this catalyst. As a result, the reaction ratio of methacrolein was 62.1%, the selectivity of methacrylic acid was 81.4%, and the yield of methacrylic acid was 50.5%.

The results in Reference Example 1, Examples 1 to 3 and Comparative Examples 1 to 4 are shown in Table 1.

TABLE 1

| | Ref. Ex. 1 | Ex. 1 | Ex. 2 | Ex. 3 | Comp. Ex. 1 | Comp. Ex. 2 | Comp. Ex. 3 | Comp. Ex. 4 |
|---|---|---|---|---|---|---|---|---|
| Retaining conditions | | | | | | | | |
| Catalyst layer temperature (° C.) | — | 20 | 15 | 30 | 15 | 30 | 15 | 30 |
| Amount of gas passing through (L/Hr) | — | 0.3 | 0.6 | 0.3 | 0.3 | 0.3 | 0.3 | 0.3 |
| Water concentration in gas (%) | — | 0.3 | about 0 | 0.2 | 0.9 | 0.9 | 0.9 | 0.9 |
| Retaining time | — | 10 days | 40 days | 20 days | 16 hrs | 10 days | 16 hrs | 10 days |
| Water content (mg/g) | 3.7 | 5.6 | 3.8 | 4.2 | 44.3 | 63.7 | 44.3 | 63.7 |
| Re-drying conditions | | | | | | | | |
| Temperature (° C.) | — | — | — | — | — | — | 280 | 280 |
| Time (Hr) | — | — | — | — | — | — | 5 | 5 |
| Water content after re-drying (mg/g) | — | — | — | — | — | — | 4.0 | 6.8 |
| Reaction results | | | | | | | | |
| Reaction ratio of methacrolein (%) | 87.8 | 87.0 | 86.6 | 86.2 | 77.4 | 60.3 | 77.7 | 62.1 |
| Selectivity of methacrylic acid (%) | 87.5 | 88.2 | 88.1 | 88.6 | 88.2 | 80.2 | 88.5 | 81.4 |
| Yield of methacrylic acid (%) | 76.8 | 76.7 | 76.3 | 76.4 | 68.3 | 48.4 | 68.8 | 50.5 |

Reference Example 2

63.52 parts of ammonium paramolybdate, 1.75 parts of ammonium metavanadate and 7.60 parts of cesium nitrate were dissolved in 200 parts of pure water at 70° C. While stirring this solution, a solution prepared by dissolving 3.55 parts of 60 wt % arsenic acid in 10 parts of pure water was added to this, further, a solution prepared by dissolving 3.46 parts of 85 wt % phosphoric acid in 10 parts of pure water was added and the mixture was heated up to 95° C. To this was added a solution prepared by dissolving 2.17 parts of copper nitrate in 10 parts of pure water and a solution prepared by dissolving 2.60 parts of cerium nitrate and 1.30 parts of lanthanum nitrate in 20 parts of pure water sequentially, and the resulted mixture was evaporated to dryness while stirring under heat. The resulted solid was, dried at 130° C. for 16 hours, then, molded under press, further, fractured, and fragments having a size of 0.85 to 1.70 mm were separated using a sieve, and thermally treated at 380° C. for 5 hours under air flow to obtain a phosphorus-molybdenum-vanadium catalyst. The element formulation of this catalyst excepting oxygen was as shown below.

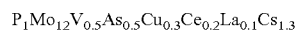

$P_1Mo_{12}V_{0.5}As_{0.5}Cu_{0.3}Ce_{0.2}La_{0.1}Cs_{1.3}$

The water content of the catalyst was 3.8 mg-$H_2O$/g-catalyst (dry).

This catalyst was filled in a stainless steel reactor having an internal diameter of 16.1 mm and a length of 600 mm, and a reaction gas composed of 6% of methacrolein, 11% of oxygen, 30% of water vapor and 53% of nitrogen was passed through under normal pressure at a reaction temperature 270° C. for a contact time of 3.6 seconds, performing a vapor phase oxidation reaction. The product was collected and analyzed, as a result, the reaction ratio of methacrolein was 89.8%, the selectivity of methacrylic acid was 87.6%, and the yield of methacrylic acid was 78.7%.

Example 4

The same catalyst as prepared in Reference Example 2 was filled in the same stainless steel reactor as used in Reference Example 2. Then, air having a water concentration of 0.5% was passed through at 0.3 L/Hr per unit catalyst weight (g) while retaining the temperature of a catalyst layer at 30° C. for 10 days. The water content of the catalyst after maintaining for 10 days was 15.2 mg-$H_2O$/g-catalyst(dry).

The same reaction was conducted as in Reference Example 2 using this catalyst. As a result, the reaction ratio of methacrolein was 89.5%, the selectivity of methacrylic acid was 88.0%, and the yield of methacrylic acid was 78.8%.

Example 5

The same catalyst as prepared in Reference Example 2 was filled in the same stainless steel reactor as used in Reference Example 2. Then, air having a water concentration of 0.9% was passed through at 0.3 L/Hr per unit catalyst weight (g) while retaining the temperature of a catalyst layer at 30° C. for 4 days. The water content of the catalyst after maintaining for 4 days was 28.5 mg-$H_2O$/g-catalyst(dry).

The same reaction was conducted as in Reference Example 2 using this catalyst. As a result, the reaction ratio of methacrolein was 89.1%, the selectivity of methacrylic acid was 87.8%, and the yield of methacrylic acid was 78.2%.

Comparative Example 5

The same catalyst as prepared in Reference Example 2 was filled in the same stainless steel reactor as used in Reference Example 2. Then, air having a water concentration of 0.5% was passed through at 0.3 L/Hr per unit catalyst weight (g) while retaining the temperature of a catalyst layer at 10° C. for 1 day. The water content of the catalyst after maintaining for 1 day was 45.3 mg-$H_2O$/g-catalyst(dry).

The same reaction was conducted as in Reference Example 2 using this catalyst. As a result, the reaction ratio of methacrolein was 78.6%, the selectivity of methacrylic acid was 86.2%, and the yield of methacrylic acid was 67.8%.

The results in Reference Example 2, Examples 4, 5 and Comparative Example 5 are shown in Table 2.

TABLE 2

|  | Ref. Ex. 2 | Ex. 4 | Ex. 5 | Comp. Ex. 5 |
|---|---|---|---|---|
| Retaining conditions |  |  |  |  |
| Catalyst layer temperature (° C.) | — | 30 | 30 | 10 |
| Amount of gas passing through (L/Hr) | — | 0.3 | 0.3 | 0.3 |
| Water concentration in gas (%) |  | 0.5 | 0.9 | 0.5 |
| Retaining time |  | 10 days | 4 days | 1 day |
| Water content (mg/g) | 3.8 | 15.2 | 28.5 | 45.3 |
| Re-drying conditions |  |  |  |  |
| Temperature (° C.) | — | — | — | — |
| Time (Hr) | — | — | — | — |
| Water content after re-drying (mg/g) | — | — | — | — |
| Reaction results |  |  |  |  |
| Reaction ratio of methacrolein (%) | 89.8 | 89.5 | 89.1 | 78.6 |
| Selectivity of methacrylic acid (%) | 87.6 | 88.0 | 87.8 | 86.2 |
| Yield of methacrylic acid (%) | 78.7 | 78.8 | 78.2 | 67.8 |

INDUSTRIAL APPLICABILITY

According to the present invention, in a process for continuously producing an objective product by a vapor phase oxidation reaction using a phosphorus-molybdenum-vanadium catalyst, deterioration before the start of the reaction of a catalyst retained in a reactor or during the stop of the reaction can be prevented by a simple method. As a result, a catalyst can be used stably over a long period.

What is claimed is:

1. A method for preserving a catalyst comprising maintaining a phosphorus-molybdenum-vanadium catalyst containing phosphorus, molybdenum and vanadium retained in a reactor under a condition of a water content of 30 mg or less per 1 g of catalyst dry weight, before the start of the reaction or during the stop of the reaction.

2. The method for preserving a catalyst according to claim 1, wherein a retaining temperature of said catalyst is 0° C. or higher and not higher than the calcination temperature in catalyst production.

3. The method for preserving a catalyst according to claim 1, wherein a retaining temperature of said catalyst is 15° C. or higher and 150° C. or lower.

4. The method for preserving a catalyst according to claim 1, wherein a water concentration in gas in said reactor is 1 vol % or less.

5. The method for preserving a catalyst according to claim 1, wherein a water concentration in gas in said reactor is 0.5 vol % or less.

6. The method for preserving a catalyst according to claim 1, wherein a retaining temperature of said catalyst is 0° C. or higher and not higher than the calcination temperature in catalyst production, and a water concentration in gas in said reactor is 1 vol % or less.

7. The method for preserving a catalyst according to claim 1, wherein a retaining temperature of said catalyst is 15° C. or higher and 150° C. or lower, and a water concentration in gas in said reactor is 0.5 vol % or less.

8. The method for preserving a catalyst according to claim 6, wherein said temperature of the catalyst is retained 0° C. or higher and not higher than the calcination temperature in catalyst production, and the gas having a water concentration of 0.8 vol % or less and containing substantially no component lowering a catalytic performance is allowed to pass through in said reactor.

9. The method for preserving a catalyst according to claim 8, wherein the gas to be passed through in the reactor is an inert gas or oxidizing gas.

10. The method for preserving a catalyst according to claim 9, wherein the gas to be passed through in the reactor is air.

11. The method for preserving a catalyst according to claim 7, wherein said temperature of the catalyst is retained 15° C. or higher and 150° C. or lower, and the gas having a water concentration of 0.5 vol % or less and containing substantially no component lowering a catalytic performance is allowed to pass through in said reactor.

12. The method for preserving a catalyst according to claim 11, wherein the gas to be passed through in the reactor is an inert gas or oxidizing gas.

13. The method for preserving a catalyst according to claim 12, wherein the gas to be passed through in the reactor is air.

14. The method for preserving a catalyst according to claim 1, wherein said phosphorus-molybdenum-vanadium catalyst is preserved in darkness under ambient conditions.

15. The method for preserving a catalyst according to claim 1, wherein said phosphorus-molybdenum-vanadium catalyst is a catalyst used in producing methacrylic acid from methacrolein by catalytic oxidation in a vapor phase.

16. The method for preserving a catalyst according to claim 14, wherein said phosphorus-molybdenum-vanadium catalyst is a catalyst used in producing methacrylic acid from methacrolein by catalytic oxidation in a vapor phase.

17. The method for preserving a catalyst according to claim 15, wherein said phosphorus-molybdenum-vanadium catalyst is represented by the following formula (I):

$$P_aMo_bV_cCu_dX_eY_fZ_gO_h \qquad (I)$$

wherein, P, Mo, V, Cu and O represent phosphorus, molybdenum, vanadium, copper and oxygen, respectively; X represents at least one element selected from the group consisting of antimony, bismuth, arsenic, germanium, zirconium, tellurium, silver, selenium, silicon, tungsten and boron; Y represents at least one element selected from the group consisting of iron, zinc, chromium, magnesium, tantalum, cobalt, manganese, barium, gallium, cerium and lanthanum; Z represents at least one element selected from the group consisting of potassium, rubidium and cesium; and a, b, c, d, e, f, g and h represent an atom ratio of each element, and when b=12, then, a=0.5 to 3, c=0.01 to 3, d=0.01 to 2, e=0 to 3, f=0 to 3, g=0.01 to 3; and h represents an atom ratio of oxygen necessary for satisfying an atomic valence of each component.

18. The method for preserving a catalyst according to claim 16, wherein said phosphorus-molybdenum-vanadium catalyst is represented by the following formula (I):

$$P_aMo_bV_cCu_dX_eY_fZ_gO_h \qquad (I)$$

wherein, P, Mo, V, Cu and O represent phosphorus, molybdenum, vanadium, copper and oxygen, respectively; X represents at least one element selected from the group consisting of antimony, bismuth, arsenic, germanium, zirconium, tellurium, silver, selenium, silicon, tungsten and boron; Y represents at least one element selected from the group consisting of iron, zinc, chromium, magnesium, tantalum, cobalt, manganese, barium, gallium, cerium and lanthanum; Z represents at least one element selected from the group consisting of potassium, rubidium and cesium; and a, b, c, d, e, f, g and h represent an atom ratio of each element, and when b=12, then, a=0.5 to 3, c=0.01 to 3, d=0.01 to 2, e=0 to 3, f=0 to 3, g=0.01 to 3; and h represents an atom ratio of oxygen necessary for satisfying an atomic valence of each component.

19. The method for preserving a catalyst according to claim 2, wherein said phosphorus-molybdenum-vanadium catalyst is a catalyst used in producing methacrylic acid from methacrolein by catalytic oxidation in a vapor phase.

20. The method for preserving a catalyst according to claim 4, wherein said phosphorus-molybdenum-vanadium catalyst is a catalyst used in producing methacrylic acid from methacrolein by catalytic oxidation in a vapor phase.

21. The method for preserving a catalyst according to claim 6, wherein said phosphorus-molybdenum-vanadium catalyst is a catalyst used in producing methacrylic acid from methacrolein by catalytic oxidation in a vapor phase.

22. The method for preserving a catalyst according to claim 7, wherein said phosphorus-molybdenum-vanadium catalyst is a catalyst used in producing methacrylic acid from methacrolein by catalytic oxidation in a vapor phase.

23. The method for preserving a catalyst according to claim 8, wherein said phosphorus-molybdenum-vanadium catalyst is a catalyst used in producing methacrylic acid from methacrolein by catalytic oxidation in a vapor phase.

24. The method for preserving a catalyst according to claim 19, wherein said phosphorus-molybdenum-vanadium catalyst is represented by the following formula (I):

$$P_aMo_bV_cCu_dX_eY_fZ_gO_h \qquad (I)$$

wherein, P, Mo, V, Cu and O represent phosphorus, molybdenum, vanadium, copper and oxygen, respectively; X represents at least one element selected from the group consisting of antimony, bismuth, arsenic, germanium, zirconium, tellurium, silver, selenium, silicon, tungsten and boron; Y represents at least one element selected from the group consisting of iron, zinc, chromium, magnesium, tantalum, cobalt, manganese, barium, gallium, cerium and lanthanum; Z represents at least one element selected from the group consisting of potassium, rubidium and cesium; and a, b, c, d, e, f, g and h represent an atom ratio of each element, and when b=12, then, a=0.05 to 3, c=0.01 to 3, d=0.01 to 2, e=0 to 3, f=0 to 3, g=0.01 to 3, and h represents an atom ratio of oxygen necessary for satisfying an atomic valence of each component.

25. The method for preserving a catalyst according to claim 20, wherein said phosphorus-molybdenum-vanadium catalyst is represented by the following formula (I):

$$P_aMo_bV_cCu_dX_eY_fZ_gO_h \qquad (I)$$

wherein, P, Mo, V, Cu and represent phosphorus, molybdenum, vanadium, copper and oxygen, respectively; X represents at least one element selected from the group consisting of antimony, bismuth, arsenic, germanium, zirconium, tellurium, silver, selenium, silicon, tungsten and boron; Y represents at least one element selected from the group consisting of iron, zinc, chromium, magnesium, tantalum, cobalt, manganese, barium, gallium, cerium and lanthanum; Z represents at least one element selected from the group consisting of potassium, rubidium and cesium; and a, b, c, d, e, f, g and h represent an atom ratio of each element, and when b=12, then, a=0.5 to 3, c=0.01 to 3, d=0.01 to 2, e=0 to 3, f=0 to 3, g=0.01 to 3, and h represents an atom ratio of oxygen necessary for satisfying an atomic valence of each component.

26. The method for preserving a catalyst according to claim 21, wherein said phosphorus-molybdenum-vanadium catalyst is represented by the following formula (I):

$$P_aMo_bV_cCu_dX_eY_fZ_gO_h \qquad (I)$$

wherein, P, Mo, V, Cu and O represent phosphorus, molybdenum, vanadium, copper and oxygen, respectively; X represents at least one element selected from the group consisting of antimony, bismuth, arsenic, germanium, zirconium, tellurium, silver, selenium, silicon, tungsten and boron; Y represents at least one element selected from the group consisting of iron, zinc, chromium, magnesium, tantalum, cobalt, manganese, barium, gallium, cerium and lanthanum; Z represents at least one element selected from the group consisting of potassium, rubidium and cesium; and a, b, c, d, e, f, g and h represent an atom ratio of each element, and when b=12, then, a=0.5 to 3, c=0.01 to 3, d=0.01 to 2, e=0 to 3, f=0 to 3, g=0.01 to 3, and h represents an atom ratio of oxygen necessary for satisfying an atomic valence of each component.

27. The method for preserving a catalyst according to claim 22, wherein said phosphorus-molybdenum-vanadium catalyst is represented by the following formula (I):

  (I)

wherein, P, Mo, V, Cu and O represent phosphorus, molybdenum, vanadium, copper and oxygen, respectively, X represents at least one element selected from the group consisting of antimony, bismuth, arsenic, germanium, zirconium, tellurium, silver, selenium, silicon, tungsten and boron, Y represents at least one element selected from the group consisting of iron, zinc, chromium, magnesium, tantalum, cobalt, manganese, barium, gallium, cerium and lanthanum, Z represents at least one element selected from the group consisting of potassium, rubidium and cesium, a, b, c, d, e, f, g and h represent an atom ratio of each element, and when b=12, then, a=0.5 to 3, c=0.01 to 3, d=0.01 to 2, e=0 to 3, f=0 to 3, g=0.01 to 3, and h represents an atom ratio of oxygen necessary for satisfying an atomic valence of each component.

28. The method for preserving a catalyst according to claim 23, wherein said phosphorusmolybdenum-vanadium catalyst is represented by the following formula (I):

  (I)

wherein, P, Mo, V, Cu and O represent phosphorus, molybdenum, vanadium, copper and oxygen, respectively; X represents at least one element selected from the group consisting of antimony, bismuth, arsenic, germanium, zirconium, tellurium, silver, selenium, silicon, tungsten and boron; Y represents at least one element selected from the group consisting of iron, zinc, chromium, magnesium, tantalum, cobalt, manganese, barium, gallium, cerium and lanthanum; Z represents at least one element selected from the group consisting of potassium, rubidium and cesium; and a, b, c, d, e, f, g and h represent an atom ratio of each element, and when b=12, then, a=0.5 to 3, c=0.01 to 3, d=0.01 to 2, e=0 to 3, f=0 to 3, g=0.01 to 3, and h represents an atom ratio of oxygen necessary for satisfying an atomic valence of each component.

* * * * *